United States Patent
Ahearn et al.

(10) Patent No.: US 7,585,640 B2
(45) Date of Patent: *Sep. 8, 2009

(54) DIAGNOSING AND MONITORING INFLAMMATORY DISEASES BY MEASURING COMPLEMENT COMPONENTS ON WHITE BLOOD CELLS

(75) Inventors: Joseph M. Ahearn, Sewickley, PA (US); Susan M. Manzi, Wexford, PA (US); Chau-Ching Liu, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 288 days.

This patent is subject to a terminal disclaimer.

(21) Appl. No.: 10/545,052

(22) PCT Filed: May 11, 2005

(86) PCT No.: PCT/US2005/016436

§ 371 (c)(1), (2), (4) Date: Oct. 10, 2006

(87) PCT Pub. No.: WO2005/111612

PCT Pub. Date: Nov. 24, 2005

(65) Prior Publication Data

US 2007/0026387 A1    Feb. 1, 2007

Related U.S. Application Data

(60) Provisional application No. 60/570,406, filed on May 11, 2004.

(51) Int. Cl.
*G01N 33/00* (2006.01)

(52) U.S. Cl. .......... 435/7.24; 435/7.1; 435/7.21; 435/372; 435/287.2; 435/967; 435/973; 436/507; 436/520; 436/546; 436/548; 436/10; 436/63; 436/172; 436/811; 436/821

(58) Field of Classification Search ............ 435/7.1, 435/7.21, 7.25, 40.51, 337, 372, 287.2, 967, 435/973, 7.24; 436/507, 520, 546, 548, 10, 436/63, 172, 811, 821; 422/61, 73
See application file for complete search history.

(56) References Cited

U.S. PATENT DOCUMENTS

| | | | |
|---|---|---|---|
| 7,361,517 B2 * | 4/2008 | Ahearn et al. | 435/7.21 |
| 7,390,631 B2 * | 6/2008 | Ahearn et al. | 435/7.25 |
| 2005/0037441 A1 | 2/2005 | Ahearn et al. | |
| 2005/0042602 A1 * | 2/2005 | Ahearn et al. | 435/5 |

FOREIGN PATENT DOCUMENTS

| WO | WO 94/10571 A1 | 11/1994 |
|---|---|---|
| WO | WO 03/022223 A2 | 3/2003 |

OTHER PUBLICATIONS

Freysdottir et al. A flow cytometric assay for measuring complement receptor 1 (CR1) and complement component C4d on erythrocytes, Journal of Immunological Methods 142: 45-52 (1991).*

(Continued)

*Primary Examiner*—Gailene R Gabel
(74) *Attorney, Agent, or Firm*—Klarquist Sparkman, LLP

(57) ABSTRACT

The invention is related to methods of diagnosing inflammatory diseases or conditions by determining levels of components of the complement pathway on the surface of white blood cells.

16 Claims, 7 Drawing Sheets

OTHER PUBLICATIONS

Buyon et al. Assessment of Disease Activity and Impending Flare in Patients with Systemic Lupus Erythematosus, Arthritis and Rheumatism, vol. 35, No. 9 (Sep. 1992).*

Sirois et al. An Enzyme-Linked Immunosorbent Assay for the Detection of Complement Components on Red Blood Cells, Am. Journ. Clin. Path. 82 (1): 67-73 (Jul. 1984).*

Senaldi, G., et al. Correlation of the activation of the fourth component of complement (C4) with disease activity in systemic lupus erythematosus, Ann. Rheum. Dis. (1988) vol. 47: 913-917.*

Alexander, Elaine, et al., "*Serum complement activation in central nervous system disease in sjogren's syndrome;*" The American Journal of Medicine, Oct. 1988, vol. 85, No. 4, abstract only.

Atkinson, J.P., et al., "*Origin of the Fourth Component of Complement Related Chido and Rodgers Blood Group Antigens;*" 1988; Compliment; vol. 5; pp. 65-76.

Bombardier, Claire, et al., "*Derivation of the SLEDAI A Disease Activity Index for Lupus Patients;*" Arthritis Rheum, Jun. 1992, vol. 35; No. 6; pp. 630-640.

Buyon, J.P., et al., "*Assessment of disease activity and impending flare in patients with systemic lupus erythematosus;*" Arthritis Rheum, 1992, vol. 35, pp. 1028-1037.

Chudwin, D., et al., "*Activation of the Alternative Complement Pathway by Red Blood Cells from Patients with Sickle Cell Disease;*" Clinical Immunology and Immunopathology, May 1994, vol. 71, No. 2, pp. 199-202.

Corvetta, Angelo, et al.; "*Low Number of Complement C3b/C4b Receptors (CR1) on Erythrocytes from Patients with Essential Mixed Cryoglobulinemia, Systemic Lupus Erythematosus and Rheumatoid Arthritis: Relationship with Disease Activity, Anticardiolipin Antibodies, Complement Activation and Therapy;*" 1981, J. Rheumatol., vol. 18, pp. 1021-1025.

Cosio, F.G., et al., "*The High prevalence of severe early post-transplant renal allograft pathology in hepatitis C positive recipients;*" Transplantation, Oct. 27, 1996, vol. 62, No. 8, abstract only.

Falk, R.J.., et al., "*Radioimmunoassay of the attack complex of complement in serum from patients with systemic lupus erythematosus;*" N. Engl. J. Med., 1985, vol. 312, pp. 1594-1599.

Freysdottir, Jona, et al.; "*A flow cytometric assay for measuring complement receptor 1 (CR1) and the complement fragments C3d and C4d on erythrocytes;*" 1991, Journal of Immunological Methods, vol. 142, pp. 45-52.

Jouvin, Marie-Helene et al.; "*Decreased Expression of C3b Receptor (CR1) on Erythrocytes of Patients with Systemic Lupus erythematosus Contrasts with Its Normal Expression in Other Systemic Diseases and Does Not Correlate with the Occurrence or Severity of SLE Nephritis;*" Complement;1986, vol. 3, pp. 88-96.

Lach-Trifilieff, Estelle, et al., "*Complement Receptor 1 (CD35) on Human Reticulocytes: Normal Express in Systemic Lupus Erythematosus and HIV-Infected Patients;*" The Journal of Immunology, vol. 162, No. 12, Jun. 1999, pp. 7549-7554.

Lamprecht, P., et al., "*Immunological and clinical follow up of hepatitis C virus associated cryoglubulinaemic vasculitis;*" Annals of the Rheumatic Diseases, Apr. 2001, vol. 60, pp. 385-390.

Liang, Matthew H., et al., "*Reliability and Validity of Six Systems for the Clinical Assessment of Disease Activity in Systemic Lupus Erythematosus,*" Arthritis Rheum, Sep. 1989, vol. 32; No. 9; pp. 1107-1118.

Manzi, Susan, et al.; "*Measurement of Erythrocyte C4d and Complement Receptor 1 in Systemic Lupus Erythematosus;*" Nov. 2004, Arthritis & Rheumatism, vol. 50, No. 11, pp. 3596-3604.

Manzi, Susan, et al.; "*Sensitivity and Specificity of Plasma and Urine Complement Split Products as Indicators of Lupus Disease Activity;*" 1996, Arthritis & Rheumatism, vol. 39, No. 7, pp. 1178-1188.

Manzi, Susan, et al.; "*New insights into complement: a mediator of injury and marker of disease activity in systemic lupus erythematosus;*" 2004, Lupus, vol. 13, pp. 1-6.

ACCN. No. 85046338 Medline. McCarthy, T., et al., "Intrauterine devices and pelvic inflammatory disease," *Australian and New Zealand Journal Of Obstretics and Gynaecology,* May 1984, vol. 24, No. 2, pp. 106-110, Abstract.

McGeer, P.L. et al.; "*Reactions of the Immune System in Chronic Degenerative Neurological Diseases;*" The Canadian Journal of Neurological Sciences; 1991, vol. 18; pp. 376-379.

ACCN. No. 90367342 Medline. Meliconi, R., et al., "Complement activation products in idiopathic pulmonary fibrosis: relevance of fragment Ba to disease severity," *Clinical Immunology and Immunopathology,* Oct. 1990, vol. 57, No. 1, pp. 64-73, Abstract.

Navratil, J.S., et al., "*Apoptosis and autoimmunity: complement deficiency and systemic lupus erythematosus revisted;*" Curr. Rheumatol. Rep., 2000, vol. 2, pp. 32-38.

Ricker, D.M., et al., "*Serum C3 levels are diagnostically more sensitive and specific for systemic lupus erythematosus activity than are serum C4 levels;*" The Lupus Nephritis Collaborative Study Group, Am. J. Kidney Dis., 1991, vol. 18, pp. 678-685.

Ross, Gordon D. et al.; "*Disease-Associated Loss of Erythrocyte Complement Receptors (CR1, C3b Receptors) in Patients with Systemic Lupus Erythematosus and other Diseases Involving Auto antibodies and/or Complement Activation;*" 1985, Journal of Immunology, vol. 135, No. 3, pp. 2005-2014.

Senaldi, G., et al., "*Correlation of the activation of the fourth component of complement (C4) with disease activity in systemic lupus erythematosus;*" Ann. Rheum. Dis., 1988, vol. 47, pp. 913-917.

Sirois, M., et al., "*An Enzyme-linked Immunosorbent Assay for the Detection of Complement Components on Red Blood Cells;*" Am. Journ. Clin. Path., Jul. 1984, vol. 82, No. 1, pp. 67-73.

Tausk, Francisco, et al., "*The Expression of C3b Receptors in the Differentiation of Discoid Lupus Erythematosus and Systemic Lupus Erythematosus;*" Arthritis and Rheumatism, Jun. 1990, vol. 33, No. 6, pp. 888-892.

Tilley, C.A., et al., "*Localisation of Chido and Rodgers Determinants to the C4d Fragment of Human C4;*" Nature; Dec. 14, 1978; vol. 276; pp. 713-715.

Tsuboi, Y. et al.; "*Increased concentration of C4d complement protein in CSF in amyotrophic lateral sclerosis;*" Neurosurgery and Psychiatry 1994, vol. 57, pp. 859-961.

Yamada, T., et al. "*Complement-activated oligodendroglia: a new pathogenic entity identified by immunostaining with antibodies to human complement proteins C3d and C4d;*" Neuroscience Letters, 1990, vol. 112, pp. 161-166.

* cited by examiner

| | T cell[a]-C4d Mean +/- SD (range) | p value | B cell[b]-C4d Mean +/- SD (range) | p value | Monocyte[c]-C4d Mean +/- SD (range) | p value |
|---|---|---|---|---|---|---|
| SLE (n=125) | 13.89 +/- 26.50 (0 - 154.0) | | 62.55 +/0 98.12 (0 - 66.30) | | 11.1 +/- 13.08 (0.58 - 60.31) | |
| Other Diseases[d] (n=45) | 1.44 +/- 1.53 (0 - 7.62) | <0.0001[e] | 11.27 +/- 9.98 (0 - 44.15) | <0.0001[e] | 3.83 +/- 2.81 (0 - 13.59) | <0.0001[e] |
| Healthy Controls (n=20) | 1.40 +/- 0.91 (0.06 - 4.12) | <0.0001[f] | 7.67 +/- 5.10 (2.39 - 25.32) | <0.0001[f] | 3.86 +/- 2.40 (1.26 - 10.75) | <0.0001[f] |

FIG. 4

| | T cell[a]-C4d Mean +/- SD (range) | p value | B cell[b]-C4d Mean +/- SD (range) | p value | Monocyte[c]-C4d Mean +/- SD (range) | P value |
|---|---|---|---|---|---|---|
| SLE (n=125) | 3.26 +/- 5.87 (0 - 52.70) | | 18.16 +/- 12.37 (0 - 70.27) | | 2.88 +/- 2.69 (0 -27.33) | |
| Other Diseases[d] (n=45) | 0.94 +/- 1.07 (0 - 5.71) | <0.00003[e] | 13.47 +/- 12.01 (0 - 56.38) | 0.36[e] | 1.96 +/- 1.34 (0 - 6.03) | <0.004[e] |
| Healthy Controls (n=20) | 0.78 +/- 0.45 (0 - 1.67) | <0.0001[f] | 7.22 +/- 2.90 (3.91 - 15.35) | <0.0001[f] | 2.4 +/- 1.39 (0.17 - 6.13) | <0.038[f] |

FIG. 5

DIAGNOSING AND MONITORING INFLAMMATORY DISEASES BY MEASURING COMPLEMENT COMPONENTS ON WHITE BLOOD CELLS

CROSS-REFERENCES TO RELATED APPLICATIONS

This application claims the benefit of U.S. Provisional Application No. 60/570,406, filed May 11, 2004, which is herein incorporated by reference for all purposes.

STATEMENT AS TO RIGHTS TO INVENTIONS MADE UNDER FEDERALLY SPONSORED RESEARCH AND DEVELOPMENT

This invention was made with government support under grant nos. 1 RO1 HL074335 and 1 P30 AR47372 awarded by the National Institutes of Health. The government may have certain rights in this invention.

FIELD OF THE INVENTION

The invention is related to methods of diagnosing inflammatory diseases or conditions by determining levels of components of the complement pathway on the surface of white blood cells.

BACKGROUND OF THE INVENTION

This invention relates to the diagnosis and/or monitoring of patients with immunologic inflammatory conditions and diseases, e.g., systemic lupus erythematosus (SLE). Inflammation is a characteristic of virtually every immune system disease or condition and every infectious disease or condition. Many chronic inflammatory conditions and diseases, i.e., immune system diseases or conditions and infectious diseases or conditions, cause damage to multiple organ systems and are difficult to diagnose. Because the symptoms of many immunologic inflammatory conditions and diseases overlap there is a great need for diagnostic methods for rapidly and reliably diagnosing and monitoring specific immune system disease and conditions. The present invention solves this and other needs.

BRIEF SUMMARY OF THE INVENTION

The present invention provides methods for diagnosing or monitoring an inflammatory disease or condition in an individual, determining the level of at least one complement pathway component on the surface of a white blood cell and comparing that determination to the level of the same complement pathway component on the surface of a white blood cell from a control or to a reference value derived from a control white blood cell.

In one aspect of the invention, the white blood cells are lymphocytes. Lymphocytes can be isolated using antibodies that recognize specific proteins on the lymphocyte, e.g., using anti-CD3, CD4, CD8 or CD19 antibodies.

In another aspect of the invention the inflammatory disease or condition is e.g., systemic lupus erythematosus (SLE), scleroderma, rheumatoid arthritis, vasculitis, myositis, serum sickness, transplant rejection, sickle cell anemia, multiple sclerosis, gout, pre-eclampsia, cardiovascular disease, and hepatitis C virus infection. The invention encompasses diagnosis of chronic forms of the above diseases.

In another aspect of the invention, the level of complement component C4d is determined and used to diagnose or monitor an inflammatory disease or condition. In some embodiments, levels one or more other complements components will be determined in combination with the C4d levels.

In another aspect of the invention, the level of complement component C3d is determined and used to diagnose or monitor an inflammatory disease or condition. In some embodiments, levels one or more other complements components will be determined in combination with the C3d levels.

In one embodiment, the inflammatory disease or condition is SLE. For SLE diagnosis, the level of complement component C4d is determined on the surface of lymphocytes. In another embodiment, C4d levels are determined on the surface of, e.g., a T lymphocyte, a B lymphocyte, or a monocyte. C4d levels can be determined using, e.g., antibodies specific for C4d. The antibodies can labeled for detection and e.g., polyclonal or monoclonal antibodies can be used.

Diagnosis of SLE can also be accomplished by determining the level of C4d on a lymphocyte in combination with at least one other complement pathway component. In one embodiment the levels of complement components C4d and C3d are determined to diagnose or monitor SLE. C4d levels can be determined as above. C3d levels can be determined using, e.g., antibodies specific for C3d. The antibodies can labeled for detection and e.g., polyclonal or monoclonal antibodies can be used.

Diagnosis of SLE can also be accomplished by determining the level of complement component C3d on the surface of lymphocytes. In another embodiment, C3d levels are determined on the surface of, e.g., a T lymphocyte, a B lymphocyte, or a monocyte. As above, C3d levels can be determined using, e.g., antibodies specific for C3d. The antibodies can labeled for detection and e.g., polyclonal or monoclonal antibodies can be used.

In another aspect, the present invention provides a kit for diagnosing or monitoring an inflammatory disease or condition in an individual. The kit can include an antibody specific for a complement component and a means for isolating a white blood cell. Generally the means for isolating a white blood cells will be an antibody specific for the white blood cell. In one embodiment, the kit includes an antibody that is specific for complement component C4d. In a further embodiment, the kit includes a second antibody specific for complement component C3d.

In another embodiment, the white blood cell is a lymphocyte and the lymphocyte is isolated using an antibody specific for the lymphocyte, e.g., anti-CD3, CD4, CD8 or CD19 antibodies. In another embodiment, the white blood cell is, e.g., a T lymphocyte, a B lymphocyte, or a monocyte.

In a further aspect the invention provides a computer readable medium, including: (a) code for receiving data corresponding to a determination of a complement component deposited on surfaces of white blood cells; (b) code for retrieving a reference value for the complement component deposited on surfaces of white blood cells of individuals; and (c) code for comparing the data in (a) with the reference value in (b).

In one embodiment of the computer readable medium, the complement component is C4d. In another embodiment of the computer readable medium, the complement component is C3d. In a further embodiment of the computer readable

BRIEF DESCRIPTION OF THE DRAWINGS

FIG. 4 provides levels of C4d on the Surface of T Lymphocytes, B Lymphocytes, and Monocytes. C4d on different types of cells were determined by a 3-color flow cytometric assay using monoclonal antibodies specific for cell-specific surface markers and C4d or isotype control immunoglobulins. Levels of C4d were calculated as specific median fluorescence intensity (SMFI)=anti-C4d median fluorescence intensity−isotype Ig median fluorescence intensity. [a]T cells were identified by electronic gating of cells positively stained by a monoclonal anti-CD3 antibody. [b]B cells were identified by electronic gating of cells positively stained by a monoclonal anti-CD19 antibody. [c]Monocytes were identified by forward and side scattering and negative staining by anti-Cd3. [d]Patients with other inflammatory diseases such as inflammatory myopathies, Sjogren's syndrome, vasculitis, Raynaud's phenomenon, and cardiovascular disease. [e]Student t test; patients with SLE vs. patients with other diseases [f]Student t test; patients with SLE vs. healthy controls.

FIG. 5 provides levels of C3d on the Surface of T Lymphocytes, B Lymphocytes, and Monocytes. C3d on different types of cells were determined by a 3-color flow cytometric assay using monoclonal antibodies specific for cell-specific surface markers and C3d or isotype control immunoglobulins. Levels of C4d were calculated as specific median fluorescence intensity (SMFI)=anti-C4d median fluorescence intensity−isotype Ig median fluorescence intensity. [a]T cells were identified by electronic gating of cells positively stained by a monoclonal anti-CD3 antibody. [b]B cells were identified by electronic gating of cells positively stained by a monoclonal anti-CD 19 antibody. [c]Monocytes were identified by forward and side scattering and negative staining by anti-Cd3. [d]Patients with other inflammatory diseases such as inflammatory myopathies, Sjogren's syndrome, vasculitis, Raynaud's phenomenon, and cardiovascular disease. [e]Student t test; patients with SLE vs. patients with other diseases [f]Student t test; patients with SLE vs. healthy controls FIG. 6 Deposition of C4d on Peripheral Blood T cells, depicts the data of FIG. 1 using a logarithmic scale on the Y-axis providing a clearer picture of the differences between the healthy controls and the diseased states.

DETAILED DESCRIPTION OF THE INVENTION

Introduction

Figure 1:
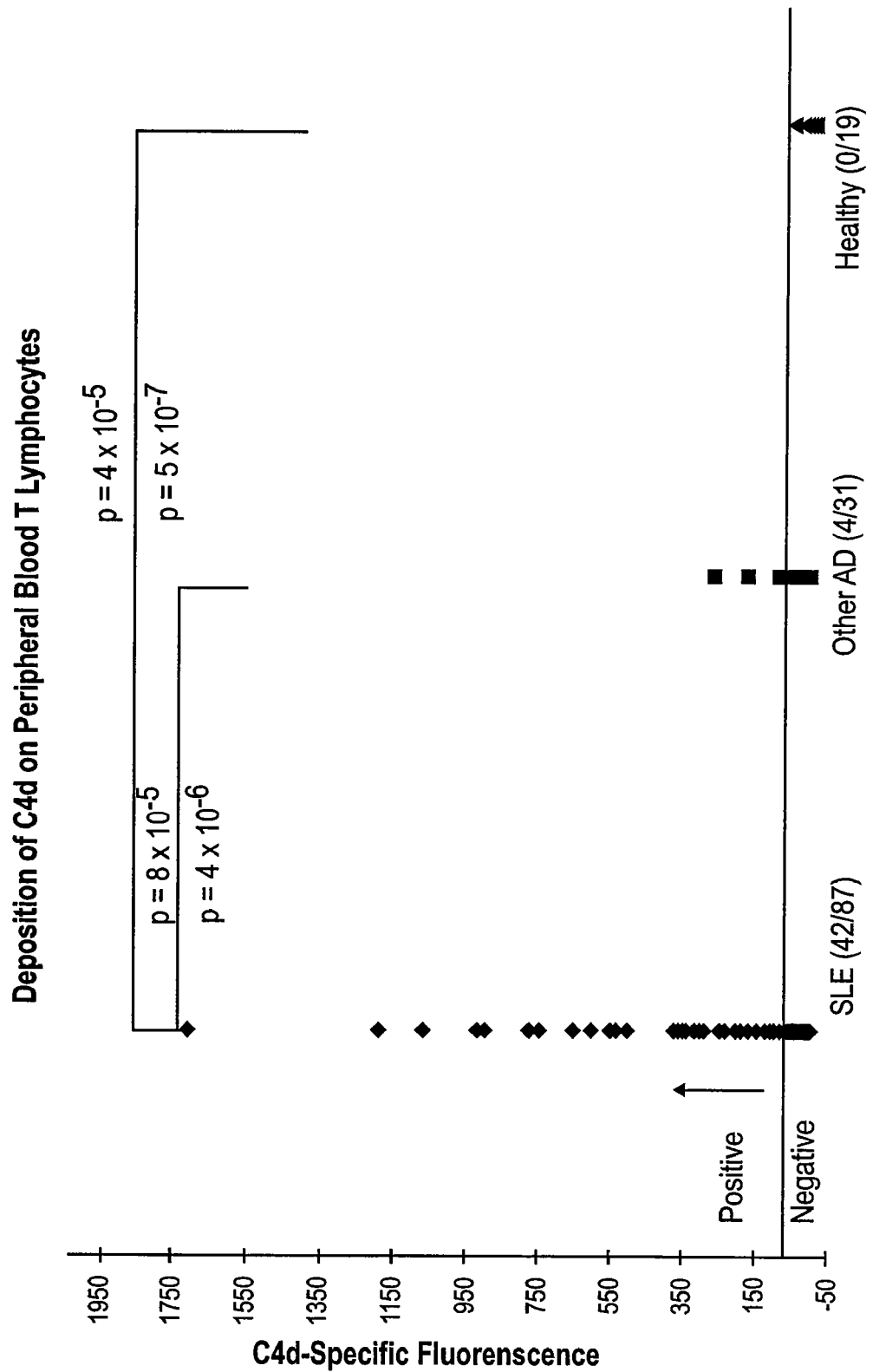
FIG. 1 demonstrates that complement pathway component C4d is deposited specifically on peripheral blood T lymphocytes of patients with SLE. Deposition of C4d on peripheral blood T lymphocytes was determined by a 2-color flow cytometric assay. T lymphocytes were identified using a FITC-conjugated monoclonal antibody specific for CD3 (a surface marker for T lymphocytes), and C4d deposited on these cells was determined using a monoclonal anti-C4d antibody followed by a PE-conjugated secondary antibody. Data shown are C4d-specific mean fluorescence (SMF) of peripheral blood T lymphocytes derived from patients with SLE (n=87, diamonds), patients with other autoimmune diseases (n=31, squares), or healthy controls (n=19, triangles). A cutpoint of specific mean fluorescence was empirically determined to distinguish individuals with C4d-positive T lymphocytes (SMF>58) from those with C4d-negative T lymphocytes (SMF<58). The frequencies of individuals with C4d-positive T lymphocytes among the groups was compared using the Chi-square test, and the p values for each pair compared are shown above the horizontal line. The mean value of C4d-specific fluorescence on T lymphocytes among the groups was compared using the Students' T test and the respective p values are shown below the horizontal line.

This disclosure provides methods of diagnosing and monitoring inflammatory diseases or conditions by determining the level of at least one complement component on the surface of a white blood cell. Previously, complement component C4d and CR1 levels on erytirocytes were determined and used to diagnose systemic lupus erythematosus (SLE) in individuals. See, e.g., WO03/022223 published Mar. 20, 2003, which is hereby incorporated by reference for all purposes. This disclosure is the first to describe diagnosing and monitoring inflammatory diseases or conditions by determining the level of at least one complement pathway component on the surface of a white blood cell.

In diagnosing the occurrence, or previous occurrence, of an inflammatory disease or condition, the level of at least one complement pathway component deposited on surfaces of white blood cells in a sample is determined. This determination is then compared with the quantities of the same complement pathway component found on the surfaces of white blood cells of individuals not having the inflammatory disease or condition.

In monitoring disease activity of a patient with an inflammatory disease or condition, a determination of at least one complement pathway component is made in the patient's blood sample, and is then compared with determinations of the quantities of the same complement pathway component on surfaces of white blood cells in a sample obtained from the same patient in the past. Comparison can also be made to quantities of the same complement pathway component found on the surfaces of white blood cells of individuals not having the inflammatory disease or condition.

The methods of this disclosure can be used to diagnosis and/or monitor SLE by determining the level of the complement pathway component C4d and/or complement component C3d on lymphocytes. Because SLE is a serious health problem, there is a need for relatively accurate and early diagnosis of this condition. Likewise, the ability to monitor the activity of this disease is of great importance. The methods of this disclosure can also be used to diagnosis and/or monitor SLE by determining the level of C4d and the level of complement pathway component C3d on lymphocytes.

In diagnosing the occurrence, or previous occurrence, of SLE, complement component C4d alone or in combination with C3d deposited on surfaces of lymphocytes in a sample is determined. This determination is then compared with the quantities of C4d and C3d found on the surfaces of lymphocytes of individuals not having SLE.

In monitoring disease activity of a patient with SLE, the same determination is made in the patient's blood sample, and is then compared with determinations of the quantities of C4d and C3d on surfaces of lymphocytes in a sample obtained from the same patient in the past. Comparison can also be made to quantities of C4d and C3d found on the surfaces of lymphocytes of individuals not having SLE.

All publications and patent applications cited in this specification are herein incorporated by reference as if each individual publication or patent application were specifically and individually indicated to be incorporated by reference.

Definitions

As used herein, an "inflammatory disease or condition" refers to any immune disease or condition that causes increased inflammation in an individual. An inflammatory disease or condition also refers to any infectious disease or condition that causes increased inflammation in an individual. In some embodiments the inflammatory disease or condition is a "chronic inflammatory disease or condition." A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. An inflammatory disease or condition includes the following: SLE, rheumatoid arthritis, vasculitis (and its specific forms such as Wegener's granulomatosis), scleroderma, myositis, serum sickness, transplant rejection, sickle cell anemia, gout, complications of pregnancy such as pre-eclampsia, multiple sclerosis, cardiovascular disease, infectious disease such as hepatitis C virus infection, etc. Each of these diseases or conditions can also be described as chronic inflammatory diseases or conditions.

As used herein a "white blood cell" refers to circulating blood cells that are not erythrocytes or reticulocytes, e.g., lymphocytes, e.g., T and B cells, NK cells, eosinophils, basophils, granulocytes, neutrophils, monocytes, macrophages, megakaryocytes, plasma cells, circulating endothelial cells, and stem cells.

As used herein a "control white blood cell" refers to a white blood cell as defined above that is isolated from an individual who does not have an inflammatory disease or condition. When an inflammatory disease or condition is being monitored in a patient, a control white blood cell can also refer to a white blood cell isolated from the same patient at an earlier time, e.g., weeks, months, or years earlier.

As used herein the "complement pathway or system" refers to a complex network of more than 30 functionally linked proteins that interact in a highly regulated manner to provide many of the effector functions of humoral immunity and inflammation, thereby serving as the major defense mechanism against bacterial and fungal infections. This system of proteins acts against invasion by foreign organisms via three distinct pathways: the classical pathway (in the presence of antibody) or the alternative pathway (in the absence of antibody) and the lectin pathway. Once activated, the proteins within each pathway form a cascade involving sequential self-assembly into multimolecular complexes that perform various functions intended to eradicate the foreign antigens that initiated the response. For a review of the complement pathway, see, e.g., Sim and Tsiftsoglou, *Biochem. Soc. Trans.* 32:21-27 (2004).

The classical pathway is usually triggered by an antibody bound to a foreign particle. It consists of several components that are specific to the classical pathway and designated C1, C4, C2. Sequentially, binding of C1q to an antigen-antibody complex results in activation of C1r and C1s (both are serine proteases), and activated C1s cleaves C4 and C2 into, respectively, C4a and C4b and C2a and C2b. Fragments C4b and C2a assemble to form C4b2a, which cleaves protein C3 into C3a and C3b, which completes activation of the classical pathway. Fragments C4b and C3b are subject to further degradation by Factor I. This factor cleaves C4b to generate C4d and also cleaves C3b, to generate iC3b followed by C3d. Thus, activation of the classical pathway of complement can lead to deposition of a number of fragments, such as C4d, iC3b, and C3d, on immune complexes or other target surfaces. Such targets include cells circulating in the blood, e.g., lymphocytes and other white blood cells, erythrocytes and platelets.

As used herein a "component of the complement pathway" includes proteins C1, C4, C2, C3 and fragments thereof, e.g., C1q, C1r, C1s, C4a, C4b, C2a, C2b, C4b2a, C3a, C3b, C4c, C4d, iC3b, C3d, C3i, C3dg. Also included are C5, C5b, C6, C7, C8, C9, C1inh, MASP2, CR1, DAF, MCP, CD59, C3aR, C5aR, C1qR, CR2, CR3, and CR4, as well as other complement pathway components, receptors and ligands not listed specifically herein.

As used herein, "systemic lupus erythematosus", "SLE", or "lupus" is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition and consequential activation of the complement system causes chronic inflammation and tissue damage.

Diagnosing and monitoring disease activity are problematic in patients with SLE. Diagnosis is problematic because of the broad spectrum of disease ranging form subtle or vague symptoms to life threatening multi-organ failure. Moreover, other inflammatory diseases with multi-system involvement can be mistaken for lupus, or vice versa. Criteria were developed for the purpose of disease classification in 1971 (Cohen, A S, et al., 1971. *Bull. Rheum. Dis.* 21:643-648) and revised in 1982 (Tan, E M, et al., 1982. *Arth. Rheum.* 25:1271-1277) and 1997 (Hochberg, M C. 1997. Arth. Rheum. 40:1725). These criteria are meant to ensure that patients from different geographic locations are comparable. Of the eleven criteria, the presence of four or more, either serially or simultaneously, is sufficient for classification of a patient as having SLE. Although these criteria serve as useful reminders of those features that distinguish SLE from other related autoimmune diseases, they are unavoidable fallible. Determining the presence or absence of the criteria often depends on physicians' interpretation and judgment. The range of clinical manifestations in SLE is much greater than that described by the eleven criteria and each manifestation can vary in the level of activity and severity from one patient to another. Furthermore, symptoms of SLE often evolve over the course of disease. There is no definitive test for SLE to date, and, thus, it is often misdiagnosed. This disclosure, however, provides efficient and accurate methods for diagnosis of SLE and other inflammatory diseases and conditions.

SLE progresses in a series of flares, or periods of acute illness, followed by remissions. The symptoms of a flare, which vary considerably between patients and even within the same patient, include malaise, fever, symmetric joint pain, and photosensitivity (development of rashes after brief sun exposure). Other symptoms of SLE include hair loss, ulcers of mucous membranes and inflammation of the lining of the heart and lungs which leads to chest pain. Red blood cells, platelets and white blood cells can be targeted in lupus, resulting in anemia and bleeding problems. More seriously, immune complex deposition and chronic inflammation in the blood vessels can lead to kidney involvement and occasionally failure requiring dialysis or kidney transplantation. Since the blood vessel is a major target of the autoimmune response in SLE, premature strokes and heart disease are not uncommon. Over time, however, these flares can lead to irreversible organ damage.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F (ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effectoer" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a component of the complement pathway or to a marker of a white blood cell, polymorphic variants, alleles, orthologs, and conservatively modified variants, or splice variants, or portions thereof, can be selected to obtain only those polyclonal antibodies that are specifically immunoreactive with the component of the complement pathway or the marker of a white blood cell and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., antibody specific for a component of the complement pathway or a marker of a white blood cell can be made detectable, e.g., by incorporating a radiolabel or fluorescent label into the antibody, and used to detect component of the complement pathway or the marker of a white blood cell specifically reactive with the labeled antibody). A labeled secondary antibody can also be used to detect an antibody specific for a component of the complement pathway or a marker of a white blood cell.

The term "contact" or "contacting" is used herein interchangeably with the following: combined with, added to, mixed with, passed over, incubated with, flowed over, etc.

The term "immunoassay" is an assay that uses an antibody to specifically bind an antigen. The immunoassay is characterized by the use of specific binding properties of a particular antibody to isolate, target, and/or quantify the antigen.

In both instances, when speaking of "determination or determining" and "quantity," we mean to include both an amount or quantity of material. When more than one complement pathway component is measured, e.g., C4d and C3d "determination or determining" and "quantity," mean in addition, or alternatively, a ratio of a first complement pathway component to a second complement pathway component, e.g., a ratio of C4d to C3d.

Determination of the Level of a Component of the Complement Pathway on a White Blood Cell.

The invention involves conducting assays on white blood cells obtained from patients to determine levels of complement pathway components. The levels of the complement components are then used to diagnose or monitor an inflammatory disease or condition in an individual.

Samples of blood are obtained from the patient and are treated with EDTA (ethylenediaminetetraacetate) to inhibit complement activation. The samples are maintained at room temperature or under cold conditions. Assays are run preferably within 24 hours.

In some embodiments the white blood cells are isolated from other components of the blood sample. For example, white blood cells (the buffy coat) can by isolated from plasma and from red blood cells by centrifugation. Each type of white blood cell can be isolated through the use of antibodies against known cell surface markers that are specific for that cell type, e.g., a lymphocyte. Antibodies against cell surface markers of white blood cells are known to those of skill and are commercially available, e.g. from BD Immunocytometry Systems. For example, cell surface markers CD3, CD4, CD8, and CD19 are specific for lymphocytes and monoclonal antibodies specific for CD3, CD4, CD8, and CD19 are available from BD Immunocytometry Systems, San Jose, Calif.

Isolation of white blood cells can be done by attaching an antibody specific to a cells surface marker to a solid support, then contacting a sample containing the white blood cells with the linked antibody. Contaminating cells are washed away allowing the isolated white blood cells to be collected.

In some embodiments, FACS is used to isolate a white blood cell, e.g., a lyphocyte. The term "FACS" refers to fluorescence activated cell sorting, a technique used to separate cells according to their content of particular molecules of interest. The molecule of interest can be specific for a type of cell or for particular cell state. The molecule of interest can be fluorescently labeled directly by binding to a fluorescent dye, or by binding to a second molecule, which has been fluorescently labeled, e.g., an antibody, lectin or aptamer that has been fluorescently labeled and that specifically binds to the molecule of interest. Thus, white blood cell specific markers can by used to isolate specific white blood cells from other cells in a blood sample.

Isolation of white blood cells also refers to gating techniques used to assay a particular cell population during flow cytometric analysis. A labeled marker specific for a white blood cell population of interest is used to analyze those cells from a population. A second labeled marker is then used to determine the level of a component of the complement pathway on the surface of the white blood cell.

The determination of the level of a component of the complement pathway may be done by a number of methods including flow cytometry, ELISA using white blood cell lysates, and radioimmunoassay. In one embodiment of this invention, the determination of the levels of a component of the complement pathway is made using flow cytometric methods, with measurements taken by direct or indirect immunofluorescence using polyclonal or monoclonal antibodies specific for the component of the complement pathway. The mean fluorescence channel (MFC) for the white blood cell component of the complement pathway is determined. Determination of complement components, e.g., C4d, CR1, and, on the surface of red blood cells or platelets is described in WO03/022223, published Mar. 20, 2003 and in U.S. Ser. No. 60/463,447, filed Apr. 16, 2003, both of which are herein incorporated by reference for all purposes.

In one embodiment, levels of the complement pathway component C4d or complement component C3d are determined on the surface of lymphocytes to diagnose or monitor the progression of SLE in individuals. The lymphocytes are isolated or detected using lymphocyte specific antibodies e.g., anti-CD3, CD4, CD8, or CD19 antibodies. In some embodiments, complement pathway component C4d and complement pathway component C3d levels are determined. Determination of C4d and C3d levels can be done by a number of methods including flow cytometry, ELISA using lymphocyte lysates, and radioimmunoassay. In one embodiment of this invention, the determination of the levels of C4d and C3d is made using flow cytometric methods, with measurements taken by direct or indirect immunofluorescence using polyclonal or monoclonal antibodies specific for C4d or C3d. The mean fluorescence channel (MFC) for lymphocyte C4d or C3d is determined. The same type of assay may be used for diagnosis or for monitoring disease activity in patients known to have SLE.

Kits

Kits for conducting the assays for both the diagnosing of inflammatory disease and monitoring of inflammatory disease activity are a part of this invention. Said kits will use any of the various reagents needed to perform the methods described herein. For example using the immunofluorescence assays, the kits will generally comprise a conjugate of a monoclonal antibody specific for complement pathway component (e.g., anti-C4d or C3d antibodies) with a fluorescent moiety, and preferably also a conjugate of a monoclonal antibody specific for a white blood cell of interest (e.g., lymphocytes using, e.g., anti-CD3, CD4, CD8, and CD19 antibodies) with a different fluorescent moiety. Additionally, the kits can comprise instructiona material for the user and such other material as may be needed in carrying out assays of this type, for example, buffers, radiolabelled antibodies, colorimeter reagents etc.

The antibodies for use in these methods and kits are known. For example, monoclonal antibodies specific for CD3, CD4, CD8, and CD19 are available from Becton Dickinson Immunocytometry Systems, San Jose, Calif. Anti-C4d and anti-C3d antibodies are available from Quidel Corp. in San Diego, Calif. and are generally described in Rogers, J., N. Cooper, et al. *PNAS* 89:10016-10020, (1992); Schwab, C. et al., *Brain. Res.* 707(2):196 (1996); Gemmell, C. *J. Biomed. Mater. Res.* 37:474-480, (1997); and, Stoltzner, S. E., et al. *Am. J. Path.* 156:489499, (2000).

Diagnostic Methods

Diagnosis of a patient with an inflammatory disease or condition is carried out by comparing the determination of complement pathway components with a base value or range of values for the quantities of the same complement pathway components typically present on the surfaces of lymphocytes in normal individuals.

For example, diagnosis of a patient with SLE is carried out by comparing the determination of C4d and/or C3d with a base value or range of values for the quantities of C4d and C3d typically present on the surfaces of lymphocytes in normal individuals. In normal individuals, low levels of C4d may occasionally be detected but C3d is not present. When using flow cytometric measurement with indirect immunofluorescence, the MFC of C4d and C3d on lymphocytes of healthy individuals ranged from 1.25 to 58.63 (mean 17.02) and −3.42 to 2.67 (mean 0.52), respectively. (Tables 1 and 3). The MFC of lymphocytes C4d and C3d in patients having SLE was higher than that of healthy individuals and ranged from −2.62 to 1057.19 (mean 201.06) and −3.95 to 318.18 (mean 62.42), respectively (Tables 2 and 3).

Monitoring of Patients

A particular feature of the methods of this invention is to indicate or reflect inflammatory activity that has occurred in the patient during the preceding several weeks or even several months. It is possible, using this procedure, to identify the occurrence of a flare-up of an inflammatory disease or condition, such as SLE, during the previous few weeks or possibly even the previous several months due to persistence of components of the complement pathway deposited on the surface of white blood cells, e.g., C4d and C3d deposited on the surface of lymphocytes.

Automation and Computer Software

The determinations of complement pathway components e.g., C4d and/or C3d, and the diagnostic and disease activity monitoring methods described above can be carried out manually, but often are conveniently carried out using an automated system and/or equipment, in which the blood sample is analyzed automatically to make the necessary determination or determinations, and the comparison with the base or reference value is carried out automatically, using computer software appropriate to that purpose.

Thus, in one aspect, the invention comprises a method for diagnosing or monitoring an inflammatory disease or condition in an individual comprising (a) automatically determining, in a blood sample from the individual containing a white blood cell of interest, complement pathway components deposited on surfaces of white blood cells in the sample, and (b) automatically comparing said determinations with reference values for the same complement pathway components on surfaces of white blood cells.

In another aspect, the invention comprises a method for diagnosing or monitoring SLE in an individual comprising (a) automatically determining, in a blood sample from the individual containing lymphocytes, complement components C4d and C3d deposited on surfaces of lymphocytes in the sample, and (b) automatically comparing said determinations with reference values for components C4d and C3d on surfaces of lymphocytes.

Computer software, or computer-readable media for use in the methods of this invention include:

(1): a computer readable medium, comprising:

code for receiving data corresponding to a determination of complement pathway components deposited on surfaces of white blood cells;

code for retrieving a reference value for the same complement pathway components deposited on surfaces of white blood cells of individuals; and code for comparing the data in (a) with the reference value of (b).

In some embodiments, computer software, or computer-readable media for diagnosing or monitoring SLE using the methods of this invention include:

(1): a computer readable medium, comprising:

code for receiving data corresponding to a determination of complement components C4d and C3d deposited on surfaces of lymphocytes;

code for retrieving a reference value for complement components C4d and C3d deposited on surfaces of lymphocytes of individuals; and code for comparing the data in (a) with the reference value of (b).

In embodiments of the invention, one or more reference values may be stored in a memory associated with a digital computer. After data corresponding to determinations of complement pathway components is obtained (e.g., from an appropriate analytical instrument), the digital computer may compare the complement pathway component data with one or more appropriate reference values. After this comparison takes place, the digital computer can automatically determine if the data corresponding to the determination of t complement pathway component is associated with an inflammatory disease or condition of interest.

In some embodiments of the invention, one or more reference values may be stored in a memory associated with a digital computer. After data corresponding to determinations of complement C4d and C3d is obtained (e.g., from an appropriate analytical instrument), the digital computer may compare the C4d and C3d data with one or more appropriate reference values. After this comparison takes place, the digital computer can automatically determine if the data corresponding to the determination of complement C4d and C3d is associated with SLE.

Accordingly, some embodiments of the invention may be embodied by computer code that is executed by a digital computer. The digital computer may be a micro, mini or large frame computer using any standard or specialized operating system such as a Windows™ based operating system. The code may be stored on any suitable computer readable media. Examples of computer readable media include magnetic, electronic, or optical disks, tapes, sticks, chips, etc. The code may also be written by those of ordinary skill in the art and in any suitable computer programming language including, C, C++, etc.

EXAMPLES AND EXPERIMENTAL DATA

The following examples are provided by way of illustration only and not by way of limitation. Those of skill will readily recognize a variety of noncritical parameters that could be changed or modified to yield essentially similar results.

Example 1

Assays of Lymphocyte C4d and C3d in Healthy Controls: Negative

Nineteen healthy individuals were studied. As shown in Table 1, C3d was not detected or barely detectable on lymphocytes of each of the nineteen healthy individuals. Samples of 3 ml of EDTA-anticoagulated peripheral blood were taken from each individual and used as a source of lymphocytes and other white blood cells. The lymphocytes were washed and resuspended in FACS buffer. Levels of C4d, C3d, and CD3 were measured by two color indirect immunofluorescence using monoclonal antibodies specific for C4d, C3d, and CD3, respectively. Levels of C4d and C3d are quantitated by flow cytometry using a FACSCalibur cytometer (Becton Dickinson). The lymphocytes were identified by forward and side scatter and CD3-fluorescence, and the mean fluorescence channel (MFC) was determined for C4d and C3d.

More particularly, blood drawn into a Vacutainer™ containing EDTA (Becton Dickinson, Franklin Lakes, N.J.) was centrifuged at 200×g. The buffy coat containing white blood cells (WBC) were carefully collected, transferred into a fresh tube, and washed with phosphate buffered saline (PBS). After removal of contaminating erythrocytes by hypotonic lysis, the remaining leukocytes were washed with PBS and immunofluorescentlyb labeled using different combinations of specific antibodies for a two-color flow cytometric analysis. Antibodies used in the initial study included: 1) antibodies specific for cell lineage markers, e.g., anti-CD3, anti-CD4, and anti-CD8 for T lymphocytes, anti-CD19 for B lymphocytes, and anti-CD14 for monocytes (BD PharMingen, San Diego, Calif.), and 2) antibodies reactive to complement C4d or C3d (Quidel, San Diego, Calif.), or the isotype control mouse IgG MOPC21. The stained cells were then analyzed using a FACSCalibur™ flow cytometer and the CellQuest™ software (Becton Dickinson Immunocytometry Systems, San Jose, Calif.). Lymphocytes were electronically gated by forward scatter properties and expression of CD3 (or CD4, CD8, CD19), specific markers for lymphocyte subsets. Nonspecific binding of immunoglobulins to lymphocytes was determined by performing identical assays in parallel using the isotype control antibody MOPC21 (obtained from ATCC). Specific binding of anti-C4d and anti-C3d were determined by subtracting the MFC obtained with MOPC21 from the MFC obtained with anti-C4d and anti-C3d respectively.

Example 2

Assays of Lymphocyte C4d/C3d to Distinguish Patients with SLE from Healthy Controls This example describes conducting assays on patients to diagnose SLE, and to establish reference values or ranges of values for complement components C4d and C3d.

For this purpose, we recruited 87 patients with SLE from our outpatient office. A single determination of lymphocyte C4d/C3d was made in 87 individuals who met ACR criteria for the diagnosis of SLE (Table 2) and in 19 healthy controls (Table 1). The mean values of C4d and C3d for patients with SLE and healthy controls are shown in Table 3. Whereas the mean value for C4d and C3d in healthy individuals was 17.02 and 0.52, respectively, the mean value for C4d and C3d among patients with SLE was 201.06 and 62.42, respectively (both p=0.0001).

TABLE 1

Levels of C4d and C3d on the Surface of Lymphocytes From Healthy Controls

| Healthy Control | C4d Level (SMFC)[a] | C3d Level (SMFC) |
| --- | --- | --- |
| 2005 | 58.23 | −2.18 |
| 2007 | 2.36 | −1.19 |
| 2008 | 7.9 | 0.35 |
| 2009 | 1.25 | 1.81 |
| 2022 | 10.45 | 1.56 |
| 2003 | 12.95 | 2.67 |
| 2034 | 2.95 | 0.45 |
| 2021 | 20.12 | −1.37 |
| 2028 | 5.66 | −1.21 |
| 2006 | 3.34 | ND[b] |
| 2013 | 7.12 | 1.62 |
| 2011 | 24.00 | −3.42 |
| 2037 | 4.91 | −1.97 |
| 2010 | 22.00 | 3.11 |
| 2025 | 37.41 | 1.57 |
| 2026 | 34.55 | 2.57 |
| 2036 | 22.86 | 1.55 |
| 2029 | 20.91 | 1.31 |
| 2035 | 24.36 | 2.22 |

[a] specific mean fluorescence channel
[b] not done

TABLE 2

Levels of C4d and C3d on the Surface of Lymphocytes from SLE Patients

| SLE Patient | C4d Level (SMFC) | C3d Level (SMFC) |
| --- | --- | --- |
| 1039 | 768.02 | 68.07 |
| 107 | 646.51 | 253.23 |
| 1078 | 12.71 | 1.53 |
| 1089 | 0.26 | −3.8 |

TABLE 2-continued

Levels of C4d and C3d on the Surface of Lymphocytes from SLE Patients

| SLE Patient | C4d Level (SMFC) | C3d Level (SMFC) |
|---|---|---|
| 1072 | 12.47 | −2.61 |
| 1012 | 31.48 | 15.65 |
| 1019 | 30.84 | −9.50 |
| 1037 | 0.04 | −3.86 |
| 1047 | 355.46 | 222.75 |
| 1003 | 894.69 | 144.30 |
| 1006 | ND | 133.26 |
| 1079 | 14.80 | 16.17 |
| 1052 | 548.01 | 216.67 |
| 1038 | 300.77 | 348.40 |
| 1063 | 20.80 | 15.09 |
| 1095 | 3.63 | 33.13 |
| 1097 | 34.73 | 25.87 |
| 1092 | 46.44 | 20.25 |
| 1016 | 352.77 | 318.28 |
| 1093 | −2.62 | 1.06 |
| 1094 | 15.49 | 6.52 |
| 1034 | 17.92 | 8.10 |
| 1066 | 540.76 | 74.75 |
| 1009 | 1183.30 | 65.33 |
| 1014 | 141.62 | 54.80 |
| 1031 | 82.67 | 64.40 |
| 1086 | 5.56 | −1.29 |
| 1098 | 16.01 | 0.29 |
| 1099 | 8.79 | 7.15 |
| 1015 | 1709.54 | 258.91 |
| 1100 | 19.99 | 18.49 |
| 1101 | 118.94 | 19.61 |
| 1102 | 191.47 | 29.13 |
| 1053 | 107.76 | 42.44 |
| 1059 | 108.89 | 106.60 |
| 1084 | 61.48 | 29.58 |
| 1103 | 43.90 | −1.74 |
| 1104 | 119.49 | 4.61 |
| 1105 | 910.93 | 202.49 |
| 1107 | 44.64 | 0.00 |
| 1109 | 40.17 | 17.67 |
| 1110 | 244.78 | 88.44 |
| 1111 | 18.05 | 5.77 |
| 1085 | 289.48 | 39.73 |
| 1043 | 6.45 | 5.46 |
| 1056 | −1.45 | −1.75 |
| 1106 | 66.56 | 12.77 |
| 1114 | 241.22 | 25.51 |
| 1017 | 166.47 | 43.17 |
| 1021 | 201.31 | 111.77 |
| 1032 | 371.08 | 77.65 |
| 1045 | 4.75 | 5.23 |
| 1115 | 57.70 | 20.08 |
| 1116 | 76.77 | 23.16 |
| 1117 | 55.45 | 9.87 |
| 1118 | 48.58 | −1.94 |
| 1030 | 50.43 | 15.72 |
| 1061 | 361.15 | 165.87 |
| 1119 | 95.70 | 29.16 |
| 1121 | 1057.19 | 263.21 |
| 1122 | 600.58 | 262.34 |
| 1124 | 23.24 | 24.69 |
| 1125 | 186.13 | 65.40 |
| 1036 | 763.59 | 185.30 |
| 1044 | 37.00 | 12.39 |
| 1055 | 19.95 | ND |
| 1126 | 235.13 | 23.29 |
| 1132 | 745.91 | 244.91 |
| 1133 | 15.36 | −1.62 |
| 1136 | 31.47 | 12.88 |
| 1137 | 314.99 | 258.50 |
| 1138 | 11.33 | 0.01 |
| 1140 | 11.98 | −0.62 |
| 1013 | 115.8 | 100.20 |
| 1082 | 339.3 | 49.31 |
| 1048 | 5.07 | −2.48 |
| 1060 | 5.96 | 3.59 |
| 1141 | 5.85 | −2.56 |
| 1142 | 17.23 | −3.95 |
| 1143 | 1.84 | 0.60 |
| 1080 | 49.98 | 32.36 |
| 1144 | −1.76 | −0.05 |
| 1145 | −0.63 | −0.67 |
| 1146 | 82.63 | 15.68 |
| 1147 | 497.35 | 227.98 |
| 1037 | 1.71 | −1.42 |
| 1150 | 202.73 | 101.35 |

Example 3

Assay of Lymphocyte C4d/C3d for Distinguishing Patients with SLE from Patients with Other Diseases These studies of patients with SLE vs. healthy controls were followed by studies to compare patients with SLE with patients diagnosed with diseases other than SLE (n=31; patients with rheumatoid arthritis, scleroderma, or inflammatory myositis). A single determination of lymphocyte C4d/C3d was made, using the same assay (Table 4). The mean values of C4d and C3d for patients with SLE, as compared with patients with other diseases are shown in Table 3. Whereas the mean value for C4d and C3d in patients with other diseases were 29.60 and 12.73, respectively, the mean value for C4d and C3d among patients with SLE was 201.06 and 62.42, respectively (both p<0.0001).

TABLE 3

Analysis of Lymphocyte C4d and C3d Levels

| | C4d Level (SMFC)[a] | | C3d Level (SMFC)[b] | |
|---|---|---|---|---|
| | mean +/− SD | range | mean +/− SD | range |
| SLE | 201.06 +/− 313.56 | −2.62-1057.19 | 62.42 +/− 89.25 | −3.95-318.18 |
| Other Diseases | 29.60 +/− 55.13 | 0-263.95 | 12.73 +/− 29.07 | −4.95-141.82 |
| Healthy Control | 17.02 +/− 14.86 | 1.25-58.23 | 0.52 +/− 1.94 | −3.42-2.67 |

*Leukocytes stained with FITC-anti-CD3 and PE-anti-C4d or PE-anti-C3d were subjected to 2-color flow cytometric analysis. CD3+ T lymphocytes were electronically gated and analyzed for the levels of C4d and C3d deposited on the surface.
[a]Specific mean fluorescence intensity (SMFC) of the C4d levels detected on CD3+ T lymphocytes
[b]SMFC of the C3d levels detected on CD3+ T lymphocytes

TABLE 4

Levels of C4d and C3d on the Surface of Lymphocytes from Patients with Other Diseases

| Other Diseases | C4d Level (SMFC) | C3d Level (SMFC) |
|---|---|---|
| 17001 | 2.88 | 0.24 |
| 13010 | 71.03 | 10.62 |
| 3042 | 10.11 | 4.91 |
| 4001 | 8.17 | −0.92 |
| 5001 | 15.83 | −0.12 |
| 6013 | 20.37 | 19.91 |
| 6008 | 10.88 | −4.95 |
| 6014 | 19.17 | 4.38 |
| 3022 | 12.92 | −4.60 |
| 4025 | 26.00 | 7.2 |
| 13032 | 25.41 | 56.25 |
| 6017 | 43.70 | 26.23 |
| 4033 | 11.97 | 3.44 |
| 4028 | 173.06 | 7.98 |
| 6011 | 9.11 | 2.20 |
| 18002 | 15.33 | 8.38 |
| 4002 | 85.99 | 16.51 |
| 8021 | 4.98 | 11.22 |
| 15005 | 1.41 | −1.71 |
| 3029 | 10.33 | 0.00 |
| 3030 | 4.41 | −3.04 |
| 3031 | 263.95 | 141.82 |
| 3032 | 0.00 | −3.12 |
| 3034 | 7.37 | 70.23 |
| 3035 | 14.01 | 9.63 |
| 4026 | 0.42 | −0.24 |
| 6002 | 2.07 | −0.52 |
| 6008 | 10.93 | 2.76 |
| 6015 | 3.98 | 0.70 |
| 4030 | 21.01 | 3.12 |
| 15003 | 10.88 | 0.76 |

Example 4

Assay of Lymphocyte C4d for Distinguishing Patients with SLE

Figure 6:
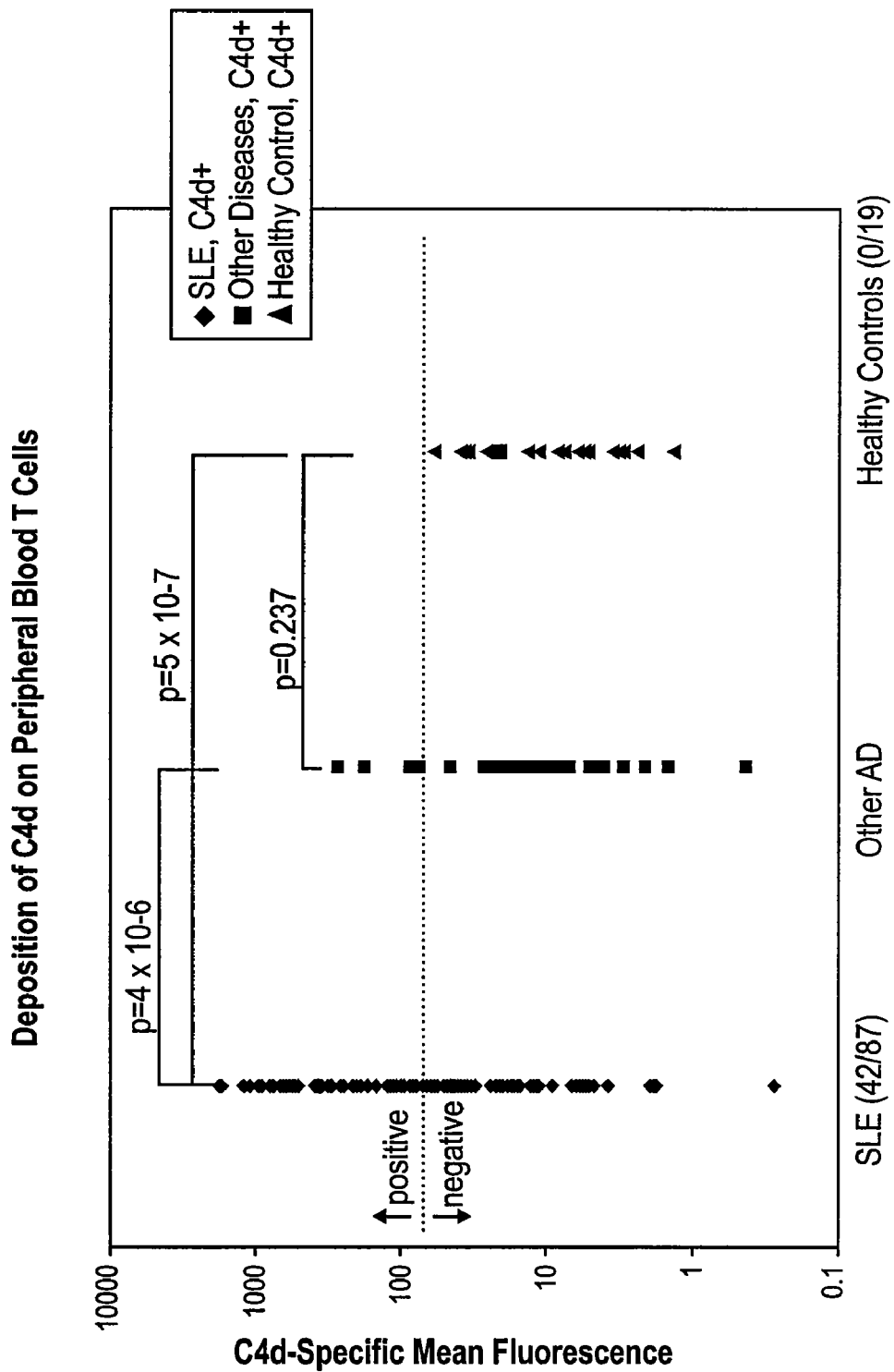

The complement pathway component C4d is deposited specifically on peripheral blood T lymphocytes of patients with SLE. Deposition of C4d on peripheral blood T lymphocytes was determined by a 2-color flow cytometric assay. T lymphocytes were identified using a FITC-conjugated monoclonal antibody specific for CD3 (a surface marker for T lymphocytes), and C4d deposited on these cells was determined using a monoclonal anti-C4d antibody followed by a PE-conjugated secondary antibody. Results are shown in FIG. 1. Data shown are C4d-specific mean fluorescence (SMF) of peripheral blood T lymphocytes derived from patients with SLE (n=87), patients with other autoimmune diseases (n=31), or healthy controls (n=19). A cutpoint of specific mean fluorescence was empirically determined to distinguish individuals with C4d-positive T lymphocytes (SMF>58) from those with C4d-negative T lymphocytes (SMF<58). While none of the healthy controls had C4d levels above the cutpoint (0/19), almost half of the SLE patients had C4d levels above the cutpoint (42/87), and some of the patients with other autoimmune diseases had C4d levels above the cutpoint (4/31). The frequencies of individuals with C4d-positive T lymphocytes among the groups was compared using the Chi-square test, and the p values for each pair compared are shown above the horizontal line. The mean value of C4d-specific fluorescence on T lymphocytes among the groups was compared using the Students' T test and the respective p values are shown below the horizontal line. FIG. 6 presents this data with a logarithmic scale on the X axis.

Example 5

Assay of Lymphocyte C3d for Distinguishing Patients with SLE and Other Inflammatory Diseases.

Figure 2:
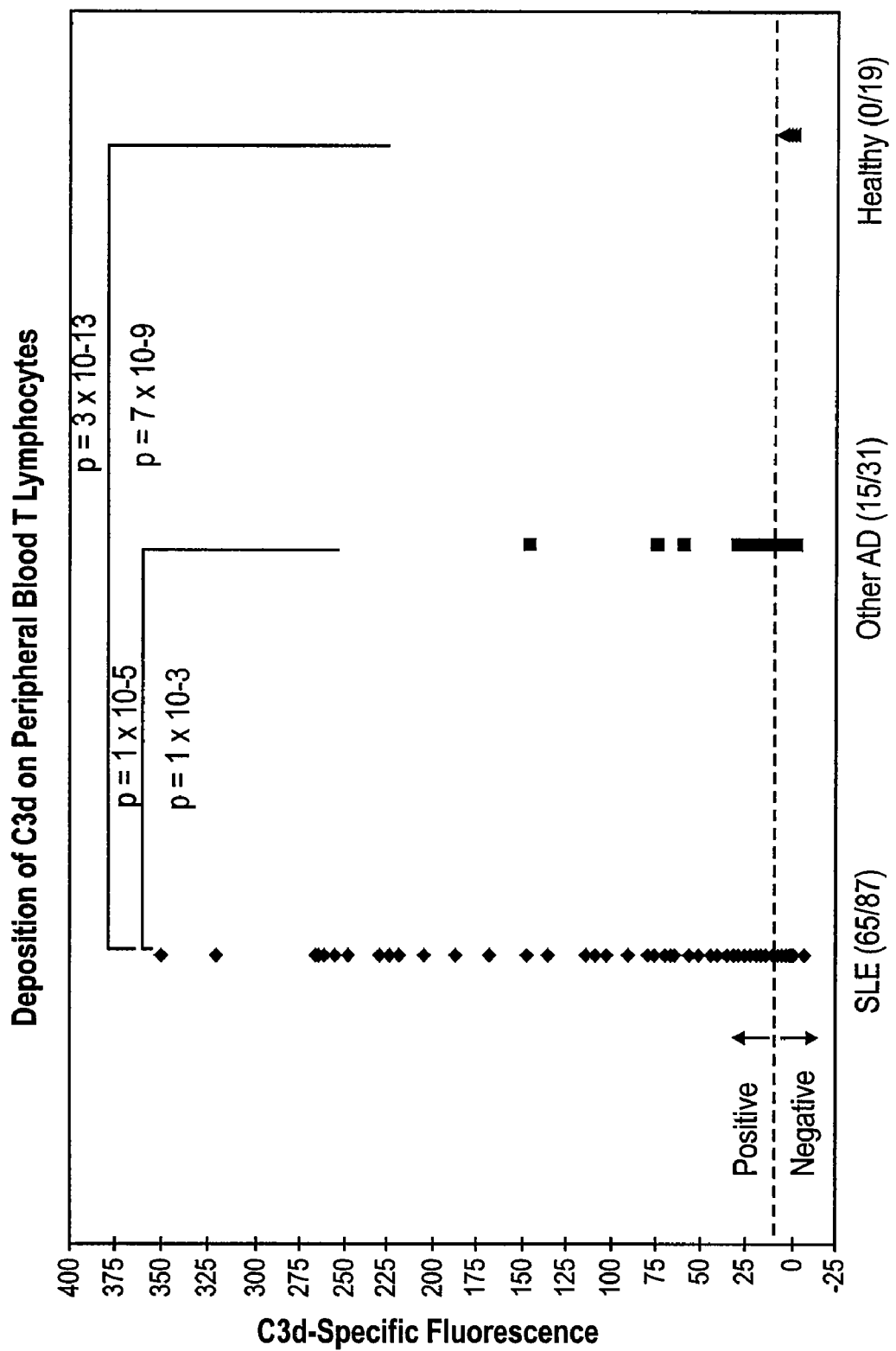
FIG. 2 demonstrates that complement pathway component C3d is deposited specifically on peripheral blood T lymphocytes of patients with SLE. Deposition of C3d on peripheral blood T lymphocytes was determined by a 2-color flow cytometric assay. T lymphocytes were identified using a FITC-conjugated monoclonal antibody specific for CD3 (a surface marker for T lymphocytes), and C3d deposited on these cells was determined using a monoclonal anti-C4d antibody followed by a PE-conjugated secondary antibody. Data shown are C3d-specific mean fluorescence of peripheral blood T lymphocytes derived from patients with SLE (n=87, diamonds), patients with other autoimmune diseases (n=31, squares), or healthy controls (n=19, triangles). A cutpoint of specific mean fluorescence was empirically determined to distinguish individuals with C3d-positive T lymphocytes (SMFC>3) from those with C3d-negative T lymphocytes (SMFC<3). The frequencies of individuals with C4d-positive T lymphocytes among the groups was compared using the Chi-square test, and the p values for each pair compared are shown above the horizontal line. The mean value of C3d-specific fluorescence on T lymphocytes among the groups was compared using the Students' T test and the respective p values are shown below the horizontal line.
Figure 7:
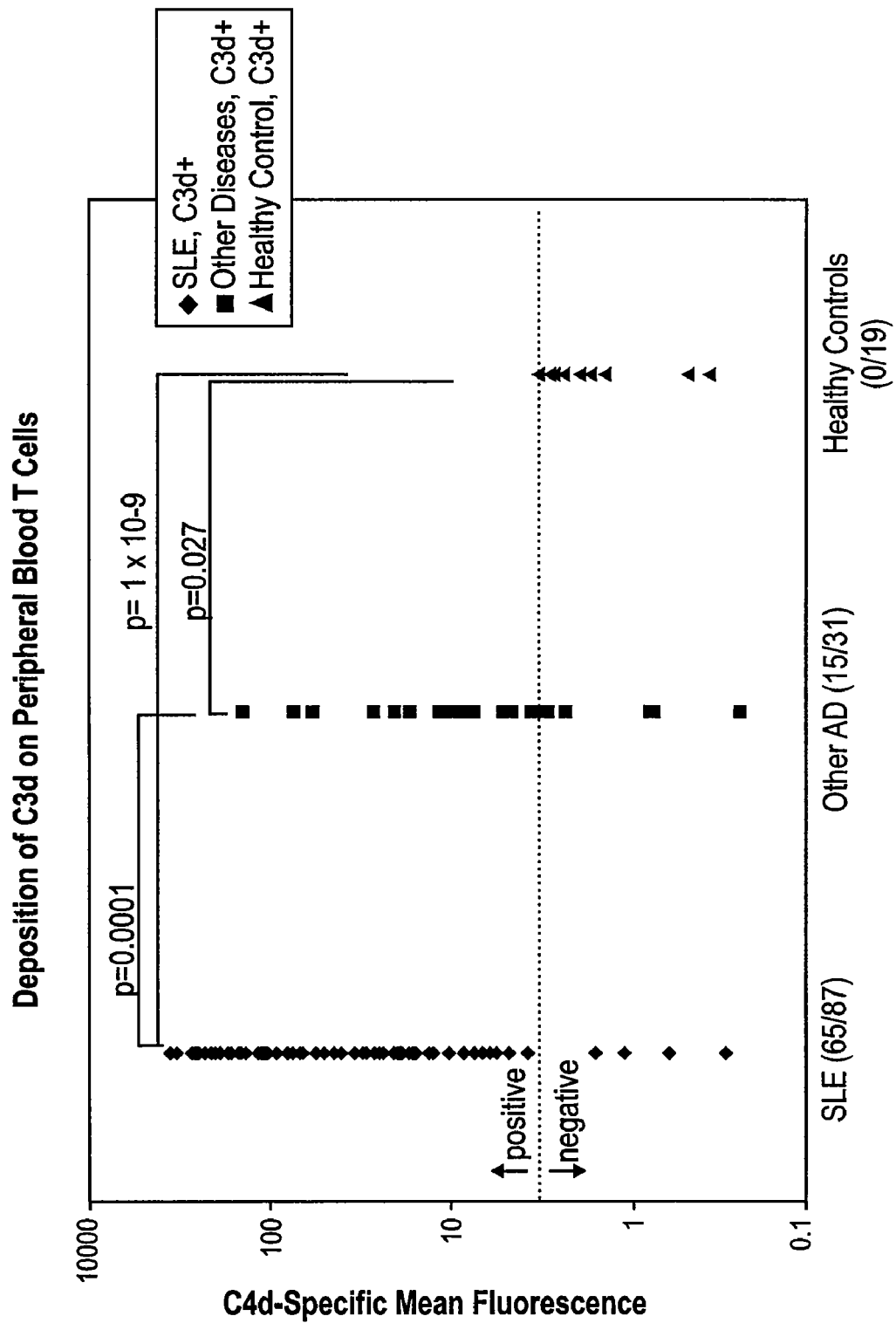
FIG. 7 Deposition of C3d on Peripheral Blood T cells, depicts the data of FIG. 2 using a logarithmic scale on the Y-axis providing a clearer picture of the differences between the healthy controls and the diseased states.

The complement pathway component C3d is deposited specifically on peripheral blood T lymphocytes of patients with SLE and on patients with other inflammatory diseases. Deposition of C3d on peripheral blood T lymphocytes was determined by a 2-color flow cytometric assay. T lymphocytes were identified using a FITC-conjugated monoclonal antibody specific for CD3 (a surface marker for T lymphocytes), and C3d deposited on these cells was determined using a monoclonal anti-C4d antibody followed by a PE-conjugated secondary antibody. Results are shown in FIG. 2. Data shown are C3d-specific mean fluorescence of peripheral blood T lymphocytes derived from patients with SLE (n=87), patients with other autoimmune diseases (n=31), or healthy controls (n=19). A cutpoint of specific mean fluorescence was empirically determined to distinguish individuals with C3d-positive T lymphocytes (SMFC>3) from those with C3d-negative T lymphocytes (SMFC<3). While none of the healthy controls had C3d levels above the cutpoint (0/19), almost 75% of the SLE patients had C3d levels above the cutpoint (65/87), and about half of the patients with other autoimmune diseases had C3d levels above the cutpoint (15/31). The frequencies of individuals with C4d-positive T lymphocytes among the groups was compared using the Chi-square test, and the p values for each pair compared are shown above the horizontal line. The mean value of C3d-specific fluorescence on T lymphocytes among the groups was compared using the Students' T test and the respective p values are shown below the horizontal line. FIG. 7 presents this data with a logarithmic scale on the X axis.

Example 6

Summary of Assays Using T-lymphocytes and Comparison to Assays Using B Lymphocytes or Monocytes.

Figure 3:
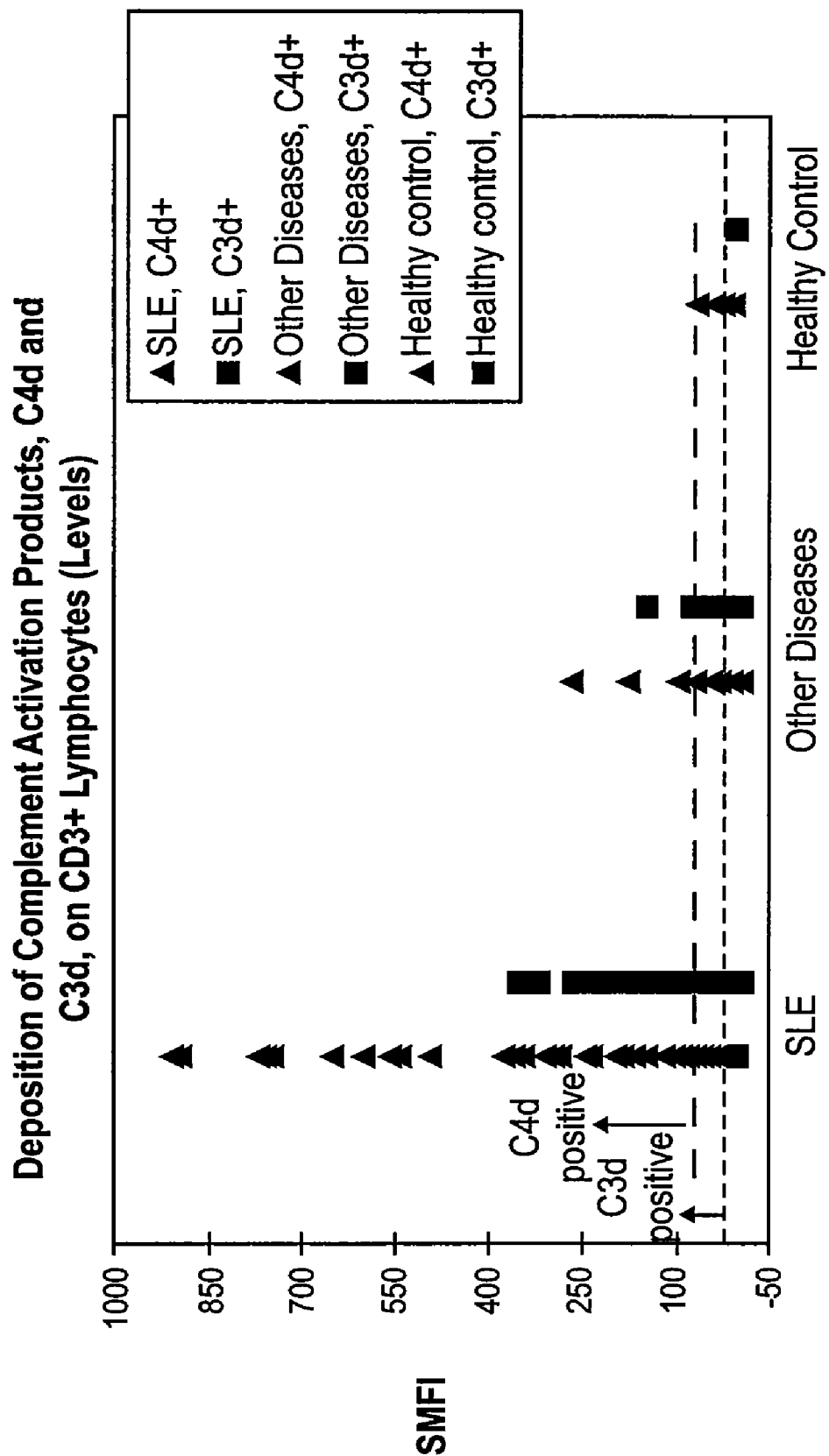
FIG. 3 demonstrates that complement ligands C4d and C3d are deposited specifically on peripheral blood T lymphocytes of patients with SLE. Deposition of C3d and C4d on peripheral blood T lymphocytes was determined by a 2-color flow cytometric assay. T lymphocytes were identified using a FITC-conjugated monoclonal antibody specific for CD3 (a surface marker for T lymphocytes), and C3d/C4d deposited on these cells was determined using a monoclonal anti-C3d (or anti-C4d) antibody, followed by a PE-conjugated secondary antibody. Data shown are C3d- and C4d-specific median fluorescence of peripheral blood T lymphocytes derived from patients with SLE (n=87), patients with other autoimmune diseases (n=31), or controls (n=19). Cutpoints of specific mean fluorescence were empirically determined to distinguish individuals with C3d-positive T lymphocytes (SMFC>3) or individuals with C4d-positive T lymphocytes (SMFI>58) from those with C3d-negative or C4d-negative T lymphocytes. The mean value of C3dspecific fluorescence on T lymphocytes among the groups was compared using the Students' T test and the respective p values are <0.0001 (not shown).

Complement ligands C4d and C3d are deposited specifically on peripheral blood T lymphocytes of patients with SLE. FIG. 3 shows deposition of C3d and C4d on peripheral blood T lymphocytes that was determined by a 2-color flow cytometric assay. T lymphocytes were identified using a FITC-conjugated monoclonal antibody specific for CD3 (a surface marker for T lymphocytes), and C3d/C4d deposited on these cells was determined using a monoclonal anti-C3d (or anti-C4d) antibody, followed by a PE-conjugated secondary antibody. Data shown are C3d- and C4d-specific median fluorescence of peripheral blood T lymphocytes derived from patients with SLE (n=87), patients with other autoimmune diseases (n=31), or healthy controls (n=19). Cutpoints of specific mean fluorescence were empirically determined to distinguish individuals with C3d-positive T lymphocytes (SMFC>3) or individuals with C4d-positive T lymphocytes (SMFI>58) from those with C3d-negative or C4d-negative T lymphocytes. The mean value of C3d specific fluorescence on T lymphocytes among the groups was compared using the Students' T test and the respective p values are <0.0001 (not shown). C4d levels were significantly higher on T lymphocytes from patients with SLE, as compared to patients with other diseases or as compared to healthy controls. C3d levels were also significantly higher on T lymphocytes from patients with SLE, as compared to patients with other diseases or as compared to healthy controls.

C4d levels were determined on the surface of T lymphocytes, B lymphocytes, and monocytes of patients with SLE, patients with other diseases, and healthy controls. C4d on different types of cells were determined by a 3-color flow cytometric assay using monoclonal antibodies specific for cell-specific surface markers and C4d or isotype control immunoglobulins. Levels of C4d were calculated as specific median fluorescence intensity (SMFI)=anti-C4d median fluorescence intensity–isotype Ig median fluorescence intensity. T cells were identified by electronic gating of cells positively stained by a monoclonal anti-CD3 antibody. B cells were identified by electronic gating of cells positively stained by a monoclonal anti-CD19 antibody. Monocytes were identified by forward and side scattering and negative staining by anti-Cd3. Patients with other inflammatory diseases such as inflammatory myopathies, Sjogren's syndrome, vasculitis, Raynaud's phenomenon, and cardiovascular disease. eStudent t test; patients with SLE vs. patients with other diseases. [C4d levels were significantly higher on T lymphocytes, B lymphocytes, and monocytes from patients with SLE, as compared to patients with other diseases or as compared to healthy controls.

C3d levels were determined on the surface of T lymphocytes, B lymphocytes, and monocytes of patients with SLE, patients with other diseases, and healthy controls. C3d on different types of cells were determined by a 3-color flow cytometric assay using monoclonal antibodies specific for cell-specific surface markers and C3d or isotype control immunoglobulins. Levels of C4d were calculated as specific median fluorescence intensity (SMFI)=anti-C4d median fluorescence intensity–isotype Ig median fluorescence intensity. T cells were identified by electronic gating of cells positively stained by a monoclonal anti-CD3 antibody. B cells were identified by electronic gating of cells positively stained by a monoclonal anti-CD19 antibody. Monocytes were identified by forward and side scattering, and negative staining by anti-Cd3. Patients with other inflammatory diseases such as inflammatory myopathies, Sjogren's syndrome, vasculitis, Raynaud's phenomenon, and cardiovascular disease. C3d levels were also significantly higher on T lymphocytes, B lymphocytes, and monocytes from patients with SLE, as compared to patients with other diseases or as compared to healthy controls.

From the figures and data, it can be seen that complement activation participates in a broad range of normal and abnormal inflammatory and immune processes. Therefore, abnormal patterns of complement activation products and complement receptors on white blood cells are useful in the diagnosis and/or monitoring of inflammatory and immune diseases other than systemic lupus erythematosus. The data in FIGS. 1-4 support this. Although the highest levels of C3d and C4d on peripheral blood T cells occurs in patients with SLE, abnormal levels of C3d are detected on T cells obtained from 15/31 (48.4%) of patients with other diseases. In addition, mean levels of C3d on T cells obtained from patients with other disease are significantly higher than mean levels of C3d on T cells obtained from healthy controls ($p=0.027$).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for diagnosing systemic lupus erythematosus (SLE) in an individual, the method comprising,
   (a) quantitating, in a blood sample from the individual, level of a C4d and/or C3d component of the complement pathway on surface of a T lymphocyte, B lymphocyte or monocyte in the sample, and
   (b) comparing the level in (a) with a level of C4d and/or C3d component of the complement pathway on surface of a control T lymphocyte, B lymphocyte or monocyte from individuals not having SLE, wherein an increased level of complement component C4d and/or C3d in the sample in (a) in comparison to the level in the control indicates that the individual has SLE.

2. The method of claim 1, wherein the T lymphocyte, B lymphocyte or monocyte is isolated using an anti-CD3 antibody.

3. The method of claim 1, wherein the level of complement component C4d is determined using an antibody specific for complement component C4d.

4. The method of claim 3, wherein the C4d antibody is labeled.

5. The method of claim 3, wherein the C4d antibody is a monoclonal antibody.

6. The method of claim 1, wherein the level of complement component C3d is determined using an antibody specific for complement component C3d.

7. The method of claim 6, wherein the C3d antibody is labeled.

8. The method of claim 6, wherein the C3d antibody is a monoclonal antibody.

9. A method for monitoring progression of systemic lupus erythematosus (SLE) in an individual, the method comprising,
   (a) quantitating in a blood sample from the individual a level of a C4d and/or C3d component of the complement pathway on surface of a T lymphocyte, B lymphocyte or monocyte in the sample, and
   (b) comparing the level in (a) with a level of C4d and/or C3d component of the complement pathway on surface of a control T lymphocyte, B lymphocyte or monocyte from a previously obtained sample of the individual, wherein a higher level of complement component C4d and/or C3d in the sample in (a) than the level in the previously obtained sample of the individual indicates progression of SLE in the individual.

10. The method of claim 9, wherein the T lymphocyte, B lymphocyte or monocyte is isolated using an anti-CD3 antibody.

11. The method of claim 9, wherein the level of complement component C4d is determined using an antibody specific for complement component C4d.

12. The method of claim 11, wherein the C4d antibody is labeled.

13. The method of claim 11, wherein the C4d antibody is a monoclonal antibody.

14. The method of claim 9, wherein the level of complement component C3d is determined using an antibody specific for complement component C3d.

15. The method of claim 14, wherein the C3d antibody is labeled.

16. The method of claim 14, wherein the C3d antibody is a monoclonal antibody.

* * * * *

UNITED STATES PATENT AND TRADEMARK OFFICE
CERTIFICATE OF CORRECTION

PATENT NO. : 7,585,640 B2  
APPLICATION NO. : 10/545052  
DATED : September 8, 2009  
INVENTOR(S) : Ahearn et al.

It is certified that error appears in the above-identified patent and that said Letters Patent is hereby corrected as shown below:

In the Specification:

Column 1, lines 17-20, "This invention was made with government support under grant nos. 1 RO1 HL074335 and 1P30 AR47372 awarded by the National Institutes of Health. The government may have certain rights in this invention" should read --This invention was made with government support under grant numbers AR047372 and HL074335, awarded by the National Institutes of Health. The government has certain rights in the invention--.

Signed and Sealed this
Second Day of July, 2013

Teresa Stanek Rea
*Acting Director of the United States Patent and Trademark Office*